United States Patent [19]

Farnworth

[11] 4,166,392

[45] Sep. 4, 1979

[54] AUTOMATIC WATER/SEWER SAMPLER

[76] Inventor: Cecil Farnworth, 31010 Bingham Rd., Birmingham, Mich. 48010

[21] Appl. No.: 914,121

[22] Filed: Jun. 9, 1978

[51] Int. Cl.² ............................................. G01N 1/12
[52] U.S. Cl. ................................................ 73/425.4 R
[58] Field of Search ........................ 73/421 B, 425.4 R

[56] References Cited

U.S. PATENT DOCUMENTS

| 2,388,548 | 11/1945 | Jurs, Jr. ............................ | 73/425.4 R |
| 3,924,471 | 12/1975 | Singer .............................. | 73/421 B |
| 4,089,209 | 5/1978 | Grana et al. ...................... | 73/425.4 R |

FOREIGN PATENT DOCUMENTS

| 41-12840 | 7/1966 | Japan ................................... | 73/425.4 |
| 483576 | 5/1975 | U.S.S.R. .............................. | 73/425.4 |

*Primary Examiner*—S. Clement Swisher

[57] ABSTRACT

An automatic water/sewer sampler, is a totally immersible, rechargeable battery powered, and of rustproof stainless and aluminum construction. It is constructed so that it may be suspended under water at a raw water inlet or from a ladder rung to hang in a sanitary sewer flow. The bottom fill feature permits taking a sample in a flow level of six inches or less. It is not affected by atmospheric pressure. The samples are collected in vacuum flasks, surrounded by insulation material to protect the biological and temperature condition of the sample until the device is returned to the Department of Public Works laboratory, for analysis. When installed in the field, the device will take a (500) milliliter sample each hour for eight hours, and the knife edge sample flask gate valve will open to accept up to half inch lumps of particulate matter and still shear through to seat and seal. The sampler also features a 'reverse cycle' in which the device may be filled with liquid chemicals or trace dyes in the laboratory to be time released at the field site.

6 Claims, 4 Drawing Figures

Fig.#1.
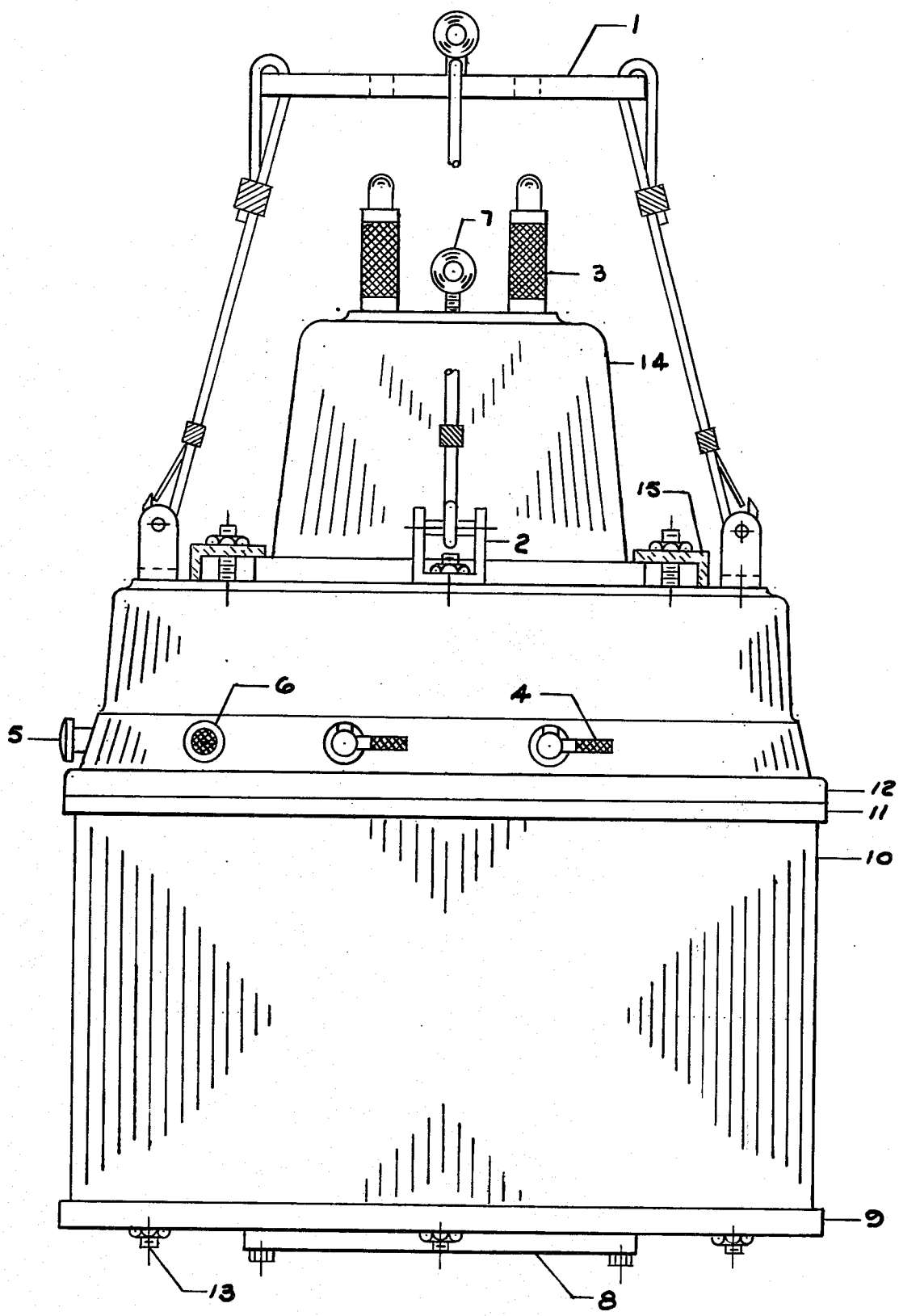

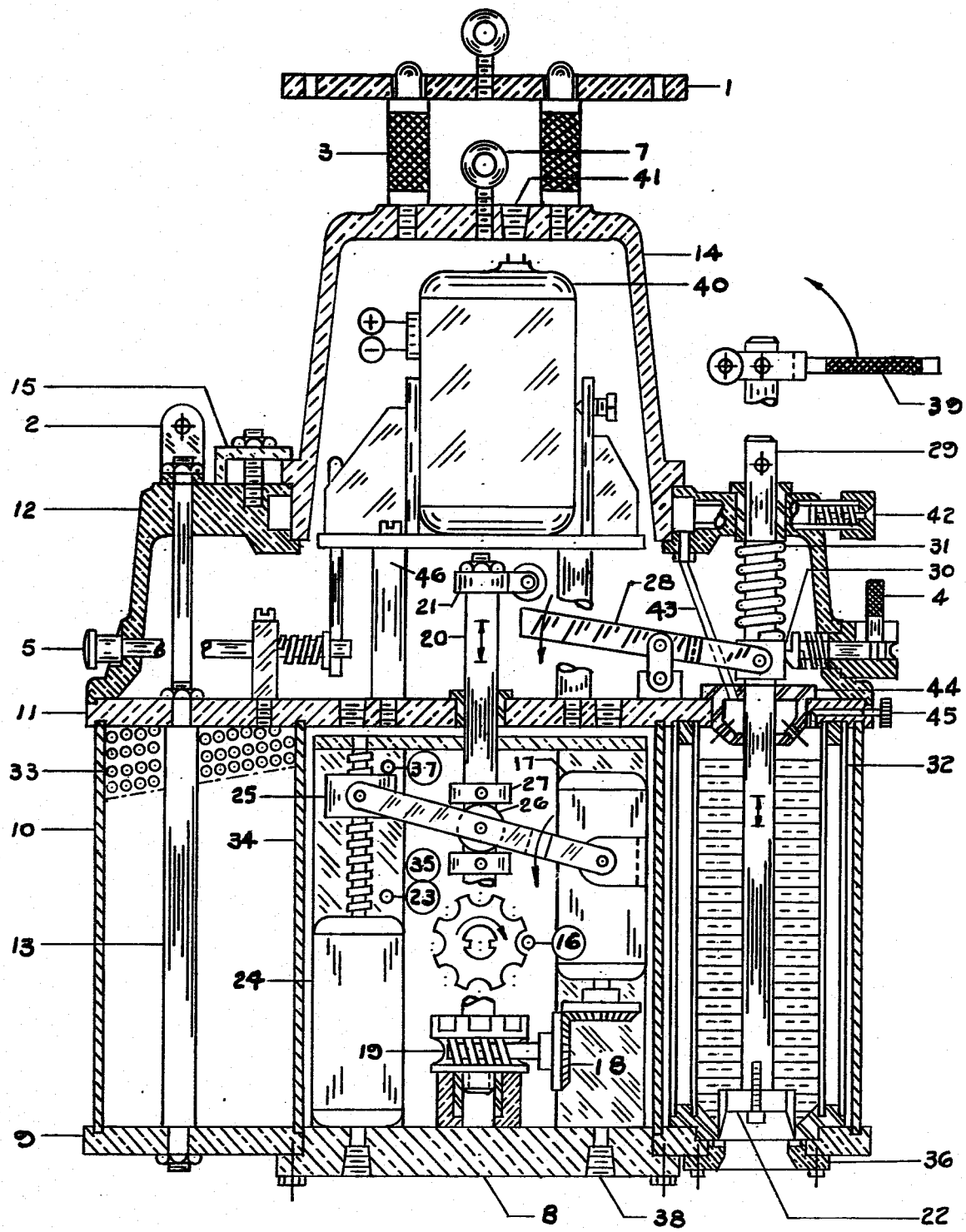
Fig #2.

Fig. #3.
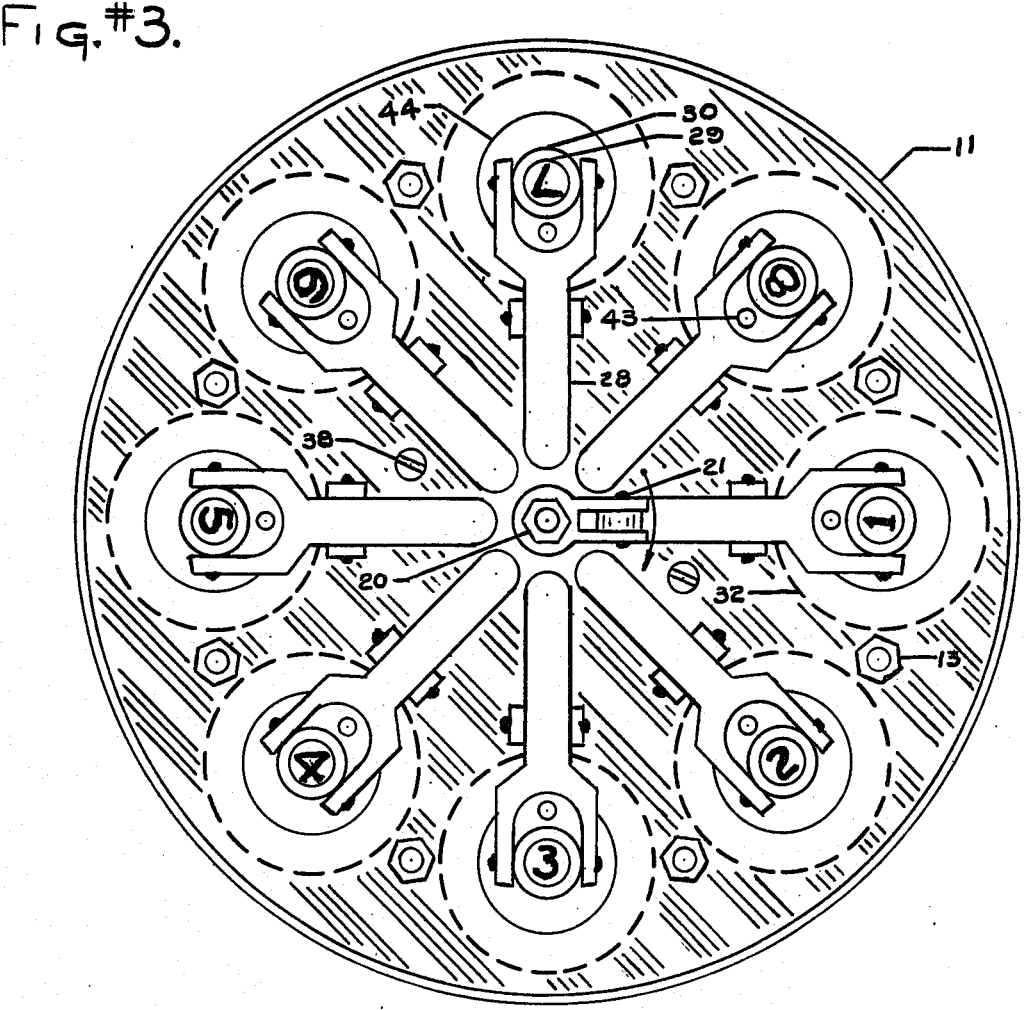
Fig. #4.
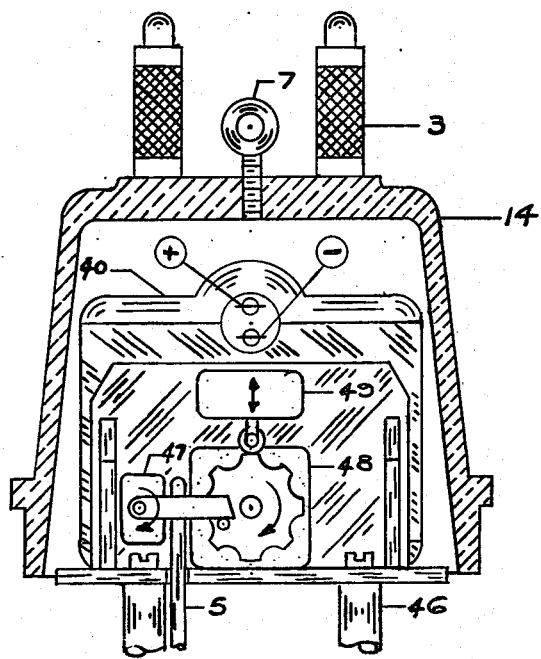

AUTOMATIC WATER/SEWER SAMPLER

The only commercially available similar function device that we are aware of is a suction device, which takes timed samples through a cluster head of one quarter inch tubes. In a sewer effluent flow, this device will plug up almost immediately. The suction is created by evacuating each sample jar, a time consuming task, and the body of the device requires a special mounting shelf in the sewer, if it is not to be left in the street to block traffic for eight hours.

The body of this competitive device is not immersible, and must be installed as close to the top of the sewer effluent flow as possible, or the limited suction available will not collect a sample. Although it is claimed that this device will take a (200) milliliter sample, a minimum amount certainly, the sales literature carefully qualifies this claim, in a 'sample volume milliliter chart' that accompanies the device when sold.

They admit that, under optimum conditions, with no particulate lumps in the sewer effluent over one quarter inch, with a vacuum gage reading of twenty inches of mercury on each sample jug, and an ambient atmospheric pressure of 28 inches of mercury, with a thirteen foot lift required, that the device is limited to taking a six milliliter sample, which in our opinion is useless. They also recommend packing cracked ice around the jugs to preserve samples.

We are aware that each function of our device can be performed by other means. For example, if a raw water inlet is conveniently located close to shore, and not out in the middle of a lake, and if twenty-four hour surveillance is required, an electronic mini-lab might well be installed to monitor and telegraph water chemical analysis conditions back to the central laboratory.

Our point here is two-fold. First, the majority of the (30,000) communities that the EPA states will require surveillance of the health and safety of water and sewer systems, could not afford the capital outlay for such a mini-lab. Second, a continuous surveillance might not be required by the lab engineers, and intermittent testing by use of this general use low-cost laboratory controlled sampler might suffice.

The multiplicity of uses for this device cannot be overstated. It will be used to detect dangerous chemicals in sewer effluent, to monitor raw water inlets as required, to monitor peak period sewer system overflow, to determine salinity and temperature of tide basin wetlands at different flow levels, to release chemicals or trace dyes at the head of spawning streams, and to detect the exact time that the giant oil tankers have flushed their tanks into our sea lanes.

BRIEF DESCRIPTION OF THE DRAWINGS

FIG. 1 is an exterior side elevation of the device as it is picked up from the laboratory ready to be suspended in the field.

FIG. 2 is a center line cross-section view, with the right hand area showing the typical construction of each of the eight station flasks, and the left hand portion, (rotated 22½ degrees), showing a typical tie bar rod construction.

FIG. 3 is a plan view in which all structural elements above the Upper Plate have been removed.

FIG. 4 is a cross-section of the Battery Cap Housing, (rotated 90 degrees from the FIG. 2 position), to exhibit the Timer Motor and the Timer Circuit components.

DESCRIPTION OF THE PREFERRED EMBODIMENT

A major advantage of this design is that no special handling equipment is required 'in transit' or in the field. Further, no Engineering Personnel is required for field installation or use. These functions are performed by Department of Public Works material handling crews.

FIG. 1 shows an exterior side elevation of the device ready to be transported to the field test site to collect raw water or sewer effluent samples.

A single hook winch one man pickup truck lifts the device, (approximately 160 lbs.), by hooking into the eyebolt of the "SUSPENSION PLATE CABLE SLING ASSEMBLY" 1. This assembly has four short wire cables terminating in lifting hooks which snap connect or disconnect to the four "HOIST BRACKETS" 2.

After lab pickup, the device is then placed on the bed of the truck for transit. At this time, the suspension plate 1 is lowered to the transit position, and the four "TRANSIT PARK POSTS" 3 engage in matching holes to support and stabilize the plate until it is necessary to hoist the device again. (see FIG. 2).

The DPW crew is requested to do three things at the test site.

First, be sure that each of the eight "FLASK HOLD OPEN LATCH" 4 knurled handles are in the open/close mode, (parallel to the base), so that each flask will cycle/seal in the field. This is a second check. The lab has already set the latches for function.

Second, one half hour before the start time for the eight hour test cycle, pull out the "START PULL ROD" 5. The "EXTERNAL INDICATOR LIGHT" 6 will light and remain lit for eight hours.

Third, lower and secure the device into the test site flow.

After eight hours, the device is retrieved, the transit handling procedure is reversed and the unit, complete with eight hourly test samples, is returned to the central lab for evaluation.

Upon arrival at the lab, the exterior is hosed clean in the yard and the transit and field use suspension plate 1 is removed by unsnapping the wire cable slings at the four hoist brackets 2, and laid aside until needed again. For handling purposes within the lab, the "BATTERY CAP EYEBOLT" 7 is used.

The structural elements, starting from the bottom of FIG. 1, are the "ACCESS AND MOUNTING PLATE ASSEMBLY" 8, which is the mounting plate for the assembly of the station actuating motors, levers, worms, etc., which are shown in subsequent views.

This mounting plate 8 seals to the "BOTTOM PLATE" 9 and may be removed to adjust switches and mechanisms, if required.

The bottom plate just mentioned is a half inch thick aluminum plate, approximately 18″ in diameter, that provides an annular groove to seat and seal the "OUTER BODY SHELL" 10, which is a 3/16″ wall thickness aluminum tubing machine turned to fit both upper and lower plate to provide a water tight seal.

The "UPPER PLATE" 11, the second 18″ diameter half inch plate used, has the same seat and seal groove as the lower plate.

The "MAIN BODY CASING" 12, as will be shown in later views, is machined to accept eight threaded "TIE RODS" 13 to hold together and seal 9, 10, 11, and 12 structural components into an integrated water tight assembly.

The "BATTERY CAP HOUSING" 14 is clamped to the above assembly timer motor circuit, (see FIG. 4), by loosening the four "BATTERY CAP HOLD DOWN CLAMPS" 15.

FIG. 2 is a center line cross section, with the right hand side showing flask operating components, and the left hand side, (rotated 22½ degrees), showing a typical tie rod construction.

One half hour after the field crew has left the test site, the device will collect the first of eight (500) milliliters samples, then continue to cycle/seal each hour for eight consecutive hours.

There are three circuits required to power the device, each of which utilize commercially available components. These individual electrical components are described and assigned detail numbers and names that identify each function.

The first circuit, (discussed in detail in FIG. 4), provides the power source and timing controls required to operate each of the two subsequent sequential circuits needed to complete each of the eight individual flask station cycles.

The second circuit provides power to the 'center post rotation' cycle, which is required to rotate the center post roller, then stop directly over the next station to function. (leave station one, index at two, leave station two, index at three, etc.)

This second circuit is energized immediately when the start pull rod 5 is pulled and power flows to the timer circuit, (see FIG. 4), and to the external indicator light 6

The current flow from the timer circuit flows through the "CENTER POST DETENTE DISC SWITCH" 16 to power a left-hand rotation for the "CENTER POST ROTATION GEAR MOTOR" 17.

This left-hand rotation is conveyed through the matched "ROTATION CYCLE BEVEL GEARS" 18 to create a right hand plan view rotation in the "CENTER POST WORM SCREW GEAR & DETENTE DISC" 19, which is slip fit keyed to the center post to allow vertical travel, while detail 19 remains at a fixed height.

The lines of the "CENTER POST" 20 are interrupted in the drawing to show a plan view of the detail 19 detente disc.

The right hand rotation of the center post continues until the roller of the "CENTER POST ROLLER BRACKET ASSEMBLY" 21 is indexed directly over the radial center line location of the next station flask.

At this exact time, the spring loaded roller of the detente disc switch 16 has seated into the next detente of 19 and shut off all power to the second circuit until the next 'center post rotation' cycle is energized by the timer circuit.

The third circuit provides power to the 'center post vertical' cycle. After the center post roller is properly positioned over the next station to function, this circuit powers the vertical travel of the center post to open and close the flasks.

When this cycle starts, the flask opens, remains open for forty seconds, then permits the spring loaded knife edge "SAMPLE FLASK GATE VALVE" 22 to seat and seal through any tramp debris.

This third circuit is energized by the timer circuit exactly one half hour after the start pull rod 5 is pulled, and the current begins to flow through the first control switch, which is the double-circuit double-break "VERTICAL TRAVEL DOWN LIMIT SWITCH" 23.

When the lever of this switch is in the 'up' position, the switch powers a right hand rotation in the "CENTER POST VERTICAL CYCLE REVERSIBLE GEAR MOTOR" 24.

The right hand rotation of the lead screw of the "VERTICAL TRAVEL LEAD SCREW & NUT ASSEMBLY" 25 starts the downward travel of the lead screw nut which is attached, with slip fit pins, to the 'arc swing' end of the "VERTICAL TRAVEL CENTER POST YOKE ASSEMBLY" 26.

The rollers of this yoke assembly are trapped, with adequate rolling clearance allowed, between two "CENTER POST SLEEVE COLLARS" 27 so that the down swing arc of the yoke assembly 26 causes the downward vertical travel of the center post 20.

As the center post roller 21 depresses the inboard end of the "FLASK OPENING LEVER YOKE" 28, the outboard end of the lever, which is slip fit pinned to the "SAMPLE FLASK CENTER POST" 29 through the "FLASK POST SPRING SEAT COLLAR" 30, rises to compress the "FLASK SEAL SEAT SPRING" 31 and lift the flask gate valve 22 and allow that particular sample flask to fill.

The "SAMPLE FLASK ASSEMBLY" 32 consists of inner and outer stainless steel tubing shells that are silver soldered into an assembly at the top by insertion of a filler ring, and at the bottom by the insertion of the combination filler ring and bottom gate shear detail.

After silver solder assembly of the flask 32, the air space between the inner and outer shell is evacuated, to create a vacuum jacketed flask effect to help maintain the temperature at which the sample was taken.

Further protection against sample temperature change is provided by filling the space between flasks with "PELLET TYPE INSULATION" 33.

This insulation is prevented from entering the central cavity occupied by the mounting plate assembly 8 by the "INNER BODY SHELL" 34 which has the same construction and purpose as the outer body shell 10 except it is smaller in diameter.

The right hand rotation continues until the lead screw nut 25 snaps the down limit switch 23 into the 'down' position, which shuts off the right hand rotation power, then snaps over to the bottom circuit which powers the left hand rotation required to permit the flask to seat and seal.

Before this current can reach the left hand rotation terminals of the reversible gear motor 24, it must pass through a "SOLID STATE TIME DELAY" 35, which delays current flow until the flasks have been held fully open for forty seconds.

This left hand rotation continues to close the flask until the gate valve 22 seats and seals against the hard rubber gasket of the "SEAL RETAINER RING ASSEMBLY" 36, and until the top surface of the lead screw nut 25 snaps open the "VERTICAL TRAVEL UP LIMIT SWITCH" 37 which terminates all power to the 'vertical travel cycle' until the timer circuit powers the cycle again.

There are four "DRAIN PLUGS" 38 provided in case of accidental spills, two in the upper plate 11 and two in the access plate 8.

After the eight hour field test cycle is complete, the unit is hosed clean, then moved inside the lab and positioned over eight standard lab beakers which are numbered to correspond to the flask station numbers stamped on the top surface of the flask posts 29.

The "LABORATORY FLASK OPENER TOOL" 39, a one sided roller pry bar lever, (shown in an extra view above the flask center post), is used to open the flask gate valve 22 and drain the samples into the beakers positioned below.

The upward motion of the flask post 29 is continued until the hold open latch 4, (knurled handle set vertical to base), engages under the bottom side of the spring seat collar 30, which holds the flask wide open until the knurled handle is turned parallel to the base again.

The lab beakers, each containing a numbered (500) milliliter sample corresponding to the exact time of day taken, are then sent to the test area of the lab for analysis.

If the "RECHARGEABLE SEALED BATTERY" 40 needs a short charge, (about every fifth trip), the threaded "BATTERY CHARGE PLUG" 41 is removed and the charger unit can remain connected before and during the draining and flush/purging of the integral flasks.

The unit is then suspended over a lab drain tank. A standard 170 degree hot water hose is connected to the unit after removal of the "FLUSH-PURGE & AIR VENT CAP" 42, (shown in section, rotated 22½ degrees toward the viewer).

This cap serves two purposes. First, to seal the flush purge connector pipe water tight in the field. Second, an integral spring loaded valve in the cap, (similar to a tire valve), relieves the air pressure that builds in the flush water distribution internal groove of the main body casting 12, and in the eight "FLUSH WATER DISTRIBUTION TUBES" 43 as the liquid sample level rises in each sample flask.

After the flush cap 42 is removed, the hose is connected and the hot water pressurizes the inside groove of the main casting 12 then flows through the eight distribution tubes 43.

The bottom end of these tubes connect, at each flask station, to the "UPPER PLATE FLASK CENTER POST BUSHING" 44.

This bushing serves two purposes.

First, it stabilizes the center post 29 in true vertical position and provides a slip fit water tight seal for the flask.

Second, the internal diameter distribution chamber directs the hot flush water through an annular row of small holes in the bottom angle of the bushing, which creates a jet-stream powerful flushing effect to clean and sterilize the integral flasks.

After the flush purge operation has been completed, replace the battery charge plug 41 and the flush purge cap 42. Next, turn the knurled handle of the flask latch 4 parallel to the base, and the gates each snap down to seat and seal.

The unit is now ready to be returned to the field test site for another eight hour cycle of sample taking.

In the event that the laboratory engineers choose to use the device for a timed distribution of liquid chemicals in the field, (rather than for collecting samples to be returned to the lab), which is a device useage labeled 'reverse cycle' in the patent claims, the following sequence of operations is performed.

First, take the sampler, which is in sample taking field ready condition, and remove the flush purge cap 42. Next, connect the chemical tank filler hose.

The liquid chemicals or trace dye will flow through the same passages as the flush water to fill each flask with (500) milliliters of liquid chemical.

A "REVERSE CYCLE AIR VENT NEEDLE VALVE" 45 is provided at each station to relieve air pressure buildup in each flask.

Second, when the flasks are full of liquid chemical, replace the flush cap 42, close the needle valves 45, and turn the hold open latches 4 in a vertical position to the base. The sampler is now ready to function 'reverse cycle' in the field.

The field crew operation for 'reverse cycle' is exactly the same as for sample taking, except they double check to be sure that the flask latches 4 remain vertical to the base.

After the start pull rod 5 is pulled, the circuits function in the same sequence as when taking samples until the hold open latch 4 engages underneath the bottom edge of the spring seat collar 30, which holds each flask wide open to permit a full distribution of the chemicals from each station.

FIG. 3 is a plan view in which all structural elements above the upper plate 11 have been removed. The purpose of this view is to establish the radial position of details previously mentioned, such as the tie rods 13, the sampler center post 20, the center post roller bracket 21, the flask opening lever yoke 28, the flask center posts 29 with station numbers stamped on the top surface, and the flask post spring seat collars 30.

The only hidden lines shown in this plan view outline the periphery of each sample flask assembly 32.

Also shown are the drain plugs 38, the flush water distribution tubes 43, and the upper plate flask post bushings 44.

FIG. 4 is a cross section of the battery cap housing 14 area, (rotated 90 degrees from the FIG. 2 view), which shows the timer motor and timer circuit components.

The power source, a rechargeable sealed battery 40, is supported and stabilized by the "BATTERY SUPPORT ASSEMBLY" 46.

The current flow from the battery is first directed to a spring loaded, (right hand rotation), "TIMER MOTOR ROTARY SWITCH" 47.

When this rotary switch circuit is closed, it directs power to three details. First to the indicator light 6. Second, to the "TIMER MOTOR & DETENTE DISC ASSEMBLY" 48. Third, it provides the hot line to feed the double-circuit double-break "ROTATION & VERTICAL CYCLE SWITCH" 49.

At the beginning of a new field cycle, all device power is 'off', since a press fit pin in the face of the right hand rotation timer motor detente disc 48 is holding the rotary switch 47 open, as shown in the FIG. 4 view.

When the start pull rod 5 is pulled, it deflects the flexible lever arm of the rotary switch up over the top of the eight hour stop pin and permits the right hand spring load to close the circuit.

When this circuit closes, as noted previously, it lights the indicator light, starts the timer motor, and provides power to the rotation and vertical cycle switch 49.

This is a double-circuit double-break switch. The upper circuit, shown energized immediately in this view, (with the switch roller on the top of a detente lobe), powers the 'center post rotation cycle' as discussed in FIG. 2.

One half hour later, when the right hand rotation of the timer motor detente disc 48 allows the roller of the cycle switch 49 to seat into a disc detente, the 'center post rotation cycle' power is shut off, and the 'center post vertical cycle', which is the lower of the two circuits in the cycle switch 49, is energized to open and close the station flasks, as described in FIG. 2.

After the device functions once an hour for eight hours, the stop pin in the face of the timer motor detente disc will again engage the lever arm of the rotary switch 47 and shut off all power to the device.

The time interval between sample cycles can be varied to suit the user by substituting a different speed timer motor assembly 48.

We are aware that similar devices have been manufactured and sold for many years. We claim that this AUTOMATIC WATER/SEWER SAMPLER features a new and novel design.

I claim:

1. In a water/sewer sampling device of the type adapted to be lowered into a body of liquid, a particular water-tight construction which consists of three major elements,
   (A) a 'lower chamber assembly', which consists of a lower plate, an upper plate, and inner and outer tubular walls which seal to both top and bottom plates to create an annular cavity in which a plurality of integral sample collector flasks are equally spaced inside the periphery of the outer shell and outside the periphery of the inner shell,
   (B) a 'main body casing' which caps and seals the lower chamber assembly when attached by tie rods and provides an air tight sealed chamber for the operating mechanisms which open and close each station sample flask valve in timed sequence,
   (C) a 'battery housing' which fits into an opening in the upper face of the main body casting and is secured in a water tight manner by clamp brackets providing space for a battery power source and the timing mechanism, whereby the aforementioned units are assembled for immersion in a test site liquid, the complete unit can be lifted or suspended by engaging a single eye bolt attached to a system of plate and cable sling supports.

2. In a water/sewer sampling device of the type adapted to be lowered into a body of liquid, a particular automatic system of operation which consists of two inter-related electric motor powered mechanisms,
   (A) a 'center post rotation mechanism' in which a pull start rod actuates a switch to direct a current flow to excite an external indicator light, to start rotation of the shaft of a timer motor, and to direct power through a timer motor switch actuated by the timer motor, whereby the timer motor switch directs power to the center post rotation motor, which motor operating through a set of bevel gears, turns a worm screw which rotates a worm gear and detente disc slip fit and keyed to the sliding center post which, the next mechanism reciprocates up and down to open and close the valve gates of the sample flasks, the centerpost having a horizontal bracket extending from one side thereof and in the 'start' position, being held at the top of its vertical travel range to create a clearance between the center post bracket and the inboard end of each of the flask opening levers, so that the bracket assembly can rotate to the next station freely, the aforementioned electric motor rotating the center post until the bracket is centered over the next flask opening lever, at which time the current flow is interrupted by another switch, actuated by the next detente of the worm gear and detente disc,
   (B) a center post vertical travel mechanism which operates after the rotation mechanism has been shut off and the timer switch has directed power to the second of the two electric motors serving to open and close the flask gate valves at each station, the motor rotating a worm screw to lower then raise a worm screw nut which is slip fit pinned to the moving end of a hinged lever yoke, the aforementioned lever yoke having two axle mounted rollers, one on each side of the center post, which are slip fit trapped between two pinned collars attached to the center post for lifting the center post, the motor being reversible, one hand rotation causing downward travel of the center post until a down limit switch directs current flow to a solid state time delay circuit to hold the flask fully open for thirty seconds before the current flow is directed to the other hand rotation leads of the motor which returns the center post to the top position of vertical travel and allows the spring loading on the flask center post and gate assembly to exert downward pressure to seat and seal the bottom fill gate of the sample flask, the downward motion of the center post causing the bracket assembly attached to the top of the center post to contact and depress the inboard end of the flask opening lever provided at each flask station, the outboard end of which is slip fit and pinned to the flask opening post and gate assembly rising to open the flask gate and permit that particular flask station to fill.

3. In a water/sewer sampling device of the type adapted to be lowered into a body of liquid, including a plurality of flasks mounted on a base with a valve in the lower end of each flask each valve being mounted upon a vertical rod extending through an upper flask bushing, each bushing including an annular passageway communicating with a plurality of holes directed to flush the interior of each flask, spring means biasing the rod and valve toward the closed position, a removable tool for manually opening each valve by moving each rod and valve to a lifted position, latch means for holding the rod in its lifted position with means for selectively deactivating each latch means, means for introducing fluid into the upper end of each flask including an inlet, a manifold and a plurality of passageways connected to the annular passageway in each bushing, so that each flask may be flushed.

4. In a water/sewer sampling device of the type adapted to be lowered into a body of liquid, integral thermally insulated collector flask assemblies, consisting of an inner and outer shell of different diameters, the inner shell being of sufficiently smaller diameter to create an annular space between the inside surface of the outer shell and the outside surface of the inner shell, this annular space and being hermetically sealed at the top and bottom and evacuated, the bottom end wall having a valve seat formed therein, the flask assembly being surrounded by pellet type insulation.

5. In a water/sewer sampling device of the type adapted to be lowered into a body of liquid, a design construction comprising a vertical tubular member for containing a sample, an annular valve seat at the lower end of the tubular member, and valve member reciprocating between open and closed positions and including an annular knife edge cooperating with said seat to slice solid material which might be lodged between the valve and the seat, thus enabling full closure of the valve, the walls of said seat being sloped downward to eliminate possible retention of stagnant water.

6. A method of using the device of claim 3 in which the device is used to dispense liquid into the test site and wherein each flask is provided with an air vent valve comprising opening the air vent valve and closing the lower valve of each flask, introducing liquid into the flasks via the manifold and passageways, closing the air vent valve, setting each latch mechanisms to engage its respective valve rod, disposing the sampler in its sampling environment and sequentially opening each valve to dispense the liquid in a timed sequence.

* * * *